United States Patent
Ma

(10) Patent No.: US 10,265,369 B2
(45) Date of Patent: Apr. 23, 2019

(54) TOPICAL DRUG FOR TREATING BREAST CANCER AND PREPARATION METHOD THEREOF

(71) Applicant: Jian Ma, Beijing (CN)

(72) Inventor: Jian Ma, Beijing (CN)

( * ) Notice: Subject to any disclaimer, the term of this patent is extended or adjusted under 35 U.S.C. 154(b) by 0 days.

(21) Appl. No.: 15/573,269

(22) PCT Filed: Feb. 26, 2016

(86) PCT No.: PCT/CN2016/074653
§ 371 (c)(1),
(2) Date: Nov. 10, 2017

(87) PCT Pub. No.: WO2016/180070
PCT Pub. Date: Nov. 17, 2016

(65) Prior Publication Data
US 2018/0099021 A1 Apr. 12, 2018

(30) Foreign Application Priority Data
May 11, 2015 (CN) .......................... 2015 1 0235048

(51) Int. Cl.
| | |
|---|---|
| *A61K 36/00* | (2006.01) |
| *A61K 36/899* | (2006.01) |
| *A61K 35/586* | (2015.01) |
| *A61P 35/00* | (2006.01) |
| *A61K 35/62* | (2006.01) |
| *A61K 35/646* | (2015.01) |

(52) U.S. Cl.
CPC .......... *A61K 36/899* (2013.01); *A61K 35/586* (2013.01); *A61K 35/62* (2013.01); *A61K 35/646* (2013.01); *A61P 35/00* (2018.01)

(58) Field of Classification Search
CPC ...................................................... A61K 36/00
See application file for complete search history.

(56) References Cited

FOREIGN PATENT DOCUMENTS

| CN | 101357205 | 2/2009 |
|---|---|---|
| CN | 101485799 | 7/2009 |
| CN | 102178818 | 9/2011 |
| CN | 102772745 | 11/2012 |
| CN | 102908581 | 2/2013 |
| CN | 104162093 | 11/2014 |
| CN | 104784562 | 7/2015 |

OTHER PUBLICATIONS

International Search Report for PCT/CN2016/074653, dated May 25, 2016, 6 pages.

*Primary Examiner* — Qiuwen Mi
(74) *Attorney, Agent, or Firm* — Nixon & Vanderhye P.C.

(57) ABSTRACT

Disclosed is a topical drug for treating breast cancer and preparation method thereof. The topical drug comprises the following ingredients in parts by weight: 5-10 parts of *Astragalus*, 3-5 parts of *Oldenlandia diffusa*, 3-5 parts of dandelion, 5-10 parts of *Lycoris radiate*, 5-8 parts of *Carapax trionycis*, 3-5 parts of *Pinellia pedatisecta*, 2-3 parts of *Acorus calamus*, 3-5 parts of *Ferula sinkiangensis*, 3-5 parts of doubleteeth pubescent angelica root, 4-6 parts of *Cryptotaenia japonica* Hassk, 3-5 parts of *Whitmania pigra* Whitman, 5-8 parts of *Wedelia chinensis*, 6-8 parts of *Echinacea purpurea*, 4-6 parts of *Folium Eriobotryae*, 3-5 parts of *Sedum sarmentosum*, 5-10 parts of *Angelicae sinensis*, 2-5 parts of *asparagus*, 2-3 parts of scorpio, 5-8 parts of *Rubia cordifolia* L., 2-3 parts of alfalfa extract, 3-5 parts of extract of Jew's ear from mulberry trees, 5-7 parts of myrrh, 3-6 parts of nutgrass galingale rhizome and 3-5 parts of pericarpium citri reticulatae viride.

9 Claims, No Drawings

TOPICAL DRUG FOR TREATING BREAST CANCER AND PREPARATION METHOD THEREOF

This application is the U.S. national phase of International Application No. PCT/CN2016/074653 filed 26 Feb. 2016, which designated the U.S. and claims priority to CN Patent Application No. 201510235048.5 filed 11 May 2015, the entire contents of each of which are hereby incorporated by reference.

FIELD OF THE INVENTION

The present invention pertains to the field of medicine, and in particular to a topical drug for treating breast cancer and preparation method thereof.

BACKGROUND OF THE INVENTION

On a global scale, the incidence of breast cancer has been on the rise since the late 1970s. 1 out of every 8 women in the United States will develop breast cancer over the course of her lifetime. Although China does not belong to countries with high incidence of breast cancer, the situation is not optimistic. In recent years, the growth rate of breast cancer incidence in China is 1-2% higher than that in countries with high incidence. The breast cancer incidence data in 2009, published by the National Cancer Center and the Disease Prevention and Control Bureau, Ministry of Health in 2012, showed that the incidence of breast cancer ranked first in female malignancies in the tumor registration areas in China.

At present, for the treatment of breast disease such as breast hyperplasia, traditional Chinese medicine is mostly used in China, while hormone preparations and vitamins are mostly used and surgery will be taken if necessary in other countries. For example, the traditional Chinese medicine include Xiaoyao Wan, Xiangfu Wan, Bazhen Yimu Wan, Xiaojin Tablet, Ru Zeng Ning Tablet and Asparagus Tablet. The western medicine include hormone drugs, such as tamoxifen and bromocriptine. And the vitamin drugs include vitamin E, vitamin B1 and vitamin B6. However, there is no specific drug for the prevention and treatment of breast cancer. The patent document with a patent publication number of CN102908581A discloses a plaster for treating breast cancer which is prepared from the following raw materials of traditional Chinese medicine: 90 grams of bupleurum, 80 grams of turmeric, 60 grams of nutgrass galingale rhizome, 60 grams of common aucklandia root, 50 grams of pangolin scales, 80 grams of vacaria seed, 50 grams of Pheretima, 80 grams of Cortex lycii radices, 90 grams of *Oldenlandia diffusa*, 60 grams of *Fructus Forsythiae*, 90 grams of *Solanum nigrum*, 60 grams of vietnamese sophora root, 90 grams of goldhair hedyotis herb, 90 grams of *Dioscorea bulbifera*, 90 grams of herba crotalariae, 50 grams of *Radix Glycyrrhizae*, 5 grams of moschus, 6 grams of borneol, 2500 grams of sesame oil and 1200 grams of *Plumbum Rubrum*. This plaster of the invention CN102908581A has significant effect for treatment breast cancer and the patients recovered quickly. This plaster is no toxic and side effect and easy to use, which can relieve the patients from pain of radiotherapy, chemotherapy, surgery and long-term medication. The patent document with a patent publication number of CN104162093A discloses a traditional Chinese medicine preparation for treating breast cancer and preparation methods thereof and the traditional Chinese medicine preparation is characterized in that its active ingredients include the following raw materials in parts by weight: 85-95 parts of *Nidus Vespae*, 85-95 parts of *Squama Manitis*, 145-155 parts of *Salvia chinensis*, 145-155 parts of vacaria seed, 145-155 parts of *Angelicae sinensis*, 145-155 parts of *Astragalus*, 145-155 parts of *Curcuma zedoaria*, 145-155 parts of *Poria cocos* and 25-35 parts of *Panax notoginseng*. The preparation methods comprise the following steps: crushing and then mixing raw materials; soaking the mixture with cold water; extracting the volatile oil by steam distillation and keep the dregs for later use; using the original medicine water to decoct dregs and collecting the solution after decocting; repeating the previous step three times and mixing the collected solution; concentrating the mixed solution to 1.5-1.6 times at temperature of 40-50° C.; mixing the concentrated solution and the volatile oil and packaging the mixture to obtained the traditional Chinese medicine preparation for treating breast cancer, which is liquid for oral use. By functional verification, this traditional Chinese medicine preparation of the invention has therapeutic effect on breast cancer. The patent document with a patent publication number of CN104162093A involves in a traditional Chinese medicine composition for treating breast cancer and the raw material medicines of the said traditional is Chinese medicine composition are 15 grams of *Angelicae sinensis*, 10 grams of Pangolin Scales, 15 grams of *FritiLlaria cirrhosa*, 10 grams of *Paeoniae Rubra*, 10 grams of *Rehmannia glutinosa Libosch*, 10 grams of vacaria seed, 10 grams of nutgrass galingale rhizome, 10 grams of *Curcuma zedoaria*, 8 grams of *Radix Platycodi*, 15 grams of Flos Carthami, 15 grams of *Coix chinensis*, 10 grams of *Boswellia carterii*, 10 grams of myrrh, 6 grams of *Glycyrrhizae Uralensis*, 10 grams of *Pseudobulbus Cremastrae*, 10 grams of lucid ganoderma and 10 grams of *radix curcumae*, by weight. This traditional Chinese medicine composition has effect of clearing heat and removing food stagnation, detumescence and detoxification, promoting blood circulation for removing blood stasis and softening hard lumps and dispelling nodes. And this traditional Chinese medicine composition has a good therapeutic effect on breast cancer.

The drugs for treating breast cancer disclosed in the above-mentioned patents have their own advantages, but they are difficult to achieve good effects in drug absorption and treatment.

DISCLOSURE OF THE INVENTION

One object of the present invention is to provide a topical drug for treating breast cancer and the preparation method thereof. The drug is used to treat breast cancer and has good absorption effect and treatment effect.

The technical solution of the present invention is as follows: a topical drug for treating breast cancer includes the following components in parts by weight:

5-10 parts of *Astragalus*, 3-5 parts of *Oldenlandia diffusa*, 3-5 parts of dandelion, 5-10 parts of *Lycoris radiate*, 5-8 parts of *Carapax trionycis*, 3-5 parts of *Pinellia pedatisecta*, 2-3 parts of *Acorus calamus*, 3-5 parts of *Ferula sinkiangensis*, 3-5 parts of doubleteeth pubescent angelica root, 4-6 parts of *Cryptotaenia japonica* Hassk, 3-5 parts of *Whitmania pigra* Whitman, 5-8 parts of *Wedelia chinensis*, 6-8 parts of *Echinacea purpurea*, 4-6 parts of *Folium Eriobotryae*, 3-5 parts of *Sedum sarmentosum*, 5-10 parts of *Angelicae sinensis*, 2-5 parts of *asparagus*, 2-3 parts of scorpio, 5-8 parts of *Rubia cordifolia* L., 2-3 parts of alfalfa extract, 3-5 parts of extract of Jew's ear from mulberry trees, 5-7 parts of myrrh, 3-6 parts of nutgrass galingale rhizome and 3-5 parts of pericarpium citri reticulatae viride.

Preferably, the topical drug for treating breast cancer includes the following components in parts by weight:

8 parts of *Astragalus*, 4 parts of *Oldenlandia diffusa*, 4 parts of dandelion, 7 parts of *Lycoris radiate*, 6 parts of *Carapax trionycis*, 4 parts of *Pinellia pedatisecta*, 2.5 parts of *Acorus calamus*, 4 parts of *Ferula sinkiangensis*, 4 parts of doubleteeth pubescent angelica root, 5 parts of *Cryptotaenia japonica* Hassk, 4 parts of *Whitmania pigra* Whitman, 6 parts of *Wedelia chinensis*, 7 parts of *Echinacea purpurea*, 5 parts of *Folium Eriobotryae*, 4 parts of *Sedum sarmentosum*, 8 parts of *Angelicae sinensis*, 3 parts of asparagus, 2 parts of scorpio, 7 parts of *Rubia cordifolia* L., 2 parts of alfalfa extract, 4 parts of extract of Jew's ear from mulberry trees, 6 parts of myrrh, 5 parts of nutgrass galingale rhizome and 5 parts of pericarpium citri reticulatae viride.

Preferably, the said topical drug for treating breast cancer also includes following auxiliary materials in parts by weight:

100-110 parts of water, 4-5 parts of glycerin, 1-1.5 parts of xanthan gum, 1-1.5 parts of vegetable oil, 1-2 parts of squalene, 5-6 parts of emulsifier, 0.5-1 parts of polysorbate-20, 0.5-1 parts of triethanolamine, 0.5-1 parts of panthenol, 0.1-0.5 parts of thymopenti and 2-3 parts of honey.

A method for preparing the topical drug for treating breast cancer includes the following steps:

(1) weighing the following components in parts by weight: 5-10 parts of *Astragalus*, 3-5 parts of *Oldenlandia diffusa*, 3-5 parts of dandelion, 5-10 parts of *Lycoris radiate*, 5-8 parts of *Carapax trionycis*, 3-5 parts of *Pinellia pedatisecta*, 2-3 parts of *Acorus calamus*, 3-5 parts of *Ferula sinkiangensis*, 3-5 parts of doubleteeth pubescent angelica root, 5-6 parts of *Cryptotaenia japonica* Hassk, 3-5 parts of *Whitmania pigra* Whitman, 5-8 parts of *Wedelia chinensis*, 6-8 parts of *Echinacea purpurea*, 4-6 parts of *Folium Eriobotryae*, 3-5 parts of *Sedum sarmentosum*, 5-10 parts of *Angelicae sinensis*, 2-5 parts of asparagus, 2-3 parts of scorpio, 5-8 parts of *Rubia cordifolia* L., 5-7 parts of myrrh, 3-6 parts of nutgrass galingale rhizome and 3-5 parts of pericarpium citri reticulatae viride; adding water to the mixture of those components, in which the weight of water is 4-5 times the weight of all the above-mentioned components; decocting the mixture for 100-150 minutes; then filtering the mixture to get the filtrate and dregs for later use;

(2) adding ethanol solution to the dregs obtained by step (1), in which the weight of ethanol solution is 4-5 times the weight of the dregs; decocting the is mixture for 120-160 minutes; then filtering it to get the filtrate and dregs for later use;

(3) heating the filtrate obtained by step (2) to 80-90° C.; and recovering the ethanol and getting the filtrate;

(4) adding acetic acid solution to the dregs obtained by step (2), in which the weight of acetic acid solution is 4-5 times the weight of the dregs; decocting the mixture for 50-70 minutes; then filtering it to get the filtrate;

(5) combining the filtrate obtained by step (1), step (3) and step (4); then adding 2-3 parts by weight of alfalfa extract and 3-5 parts by weight of extract of Jew's ear from mulberry trees to the combined filtrate; heating and stirring the mixed solution at 40-50° C. until the weight of the mixed solution is 1.5-2 times the weight of all herbs;

(6) weighing 100-110 parts by weight of water, 4-5 parts by weight of glycerin and 1-1.5 parts by weight of xanthan gum; dissolving and mixing them together; heating the solution to 80° C.; dissolving and mixing;

(7) weighing 1-1.5 parts by weight of vegetable oil, 1-2 parts by weight of squalene, 5-6 parts by weight of emulsifier, 0.5-1 parts by weight of polysorbate-20, 0.5-1 parts by weight of triethanolamine and 0.5-1 parts by weight of panthenol; mixing them; then heating the mixed solution to 80° C.;

(8) mixing the solution obtained by step (6) and step (7) and stirring evenly; when the mixture being cooled to 40-50° C., adding 2-3 parts by weight of honey and stirring evenly; then keeping the mixed solution at the current temperature for 20-25 minutes;

(9) mixing the solution obtained by step (5) and step (8); then keeping stirring the mixture until its temperature falls to room temperature; and

(10) standing the solution obtained by step (9) stable, then testing and filling to obtain the finished product.

Preferably, in step (1), the mixture is soaked at room temperature for 20-25 minutes after adding 4-5 times water to it; then the mixture is decocted at 80-90° C. for 100-150 minutes.

Preferably, in step (2), the concentration of the ethanol solution is 50-60% and the decocting temperature is 60-70° C.

Preferably, in step (4), the concentration of the acetic acid solution is 15-18% and the decocting temperature is 40-50° C.

Preferably, in step (5), the temperature of the solution obtained by step (1) and step (3) is reduced down to room temperature; then the above filtrate is combined with the solution obtained by step (4).

Preferably, the solution obtained by step (5) is treated with small molecule cutting technology to retain its activity and effectiveness simultaneously.

The beneficial effects of the invention are as follows: the material is from Chinese medicine herb and the side effect is small; by using a variety of methods to extract the active ingredients and controlling the temperature and time in the process simultaneously to retain the activity every active ingredient; auxiliary materials on the one hand make the medicine easy to smear, on the other hand promote drug performance and strengthen the efficacy; the drug can be applied directly to the skin surface, and by using small molecule cutting technology, active ingredients can be quickly absorbed through the skin, and be targeted to reach the desired site to reduce inflammation, relieve pain, promote blood circulation to remove stasis, resolve hard lump and reduce the recurrence rate of breast cancer metastasis; the drug can work efficiently and quickly.

MODE OF CARRYING OUT THE INVENTION

Example 1

A topical drug for treating breast cancer comprises the following components in parts by weight:

5 parts of *Astragalus*, 3 parts of *Oldenlandia diffusa*, 3 parts of dandelion, 5 parts of *Lycoris radiate*, 5 parts of *Carapax trionycis*, 3 parts of *Pinellia pedatisecta*, 2 parts of *Acorus calamus*, 3 parts of *Ferula sinkiangensis*, 3 parts of doubleteeth pubescent angelica root, 4 parts of *Cryptotaenia japonica* Hassk, 3 parts of *Whitmania pigra* Whitman, 5 parts of *Wedelia chinensis*, 6 parts of *Echinacea purpurea*, 4 parts of *Folium Eriobotryae*, 3 parts of *Sedum sarmentosum*, 5 parts of *Angelicae sinensis*, 2 parts of asparagus, 2 parts of scorpio, 5 parts of *Rubia cordifolia* L., 2 parts of alfalfa extract, 3 parts of extract of Jew's ear from mulberry trees, 5 parts of myrrh, 3 parts of nutgrass galingale rhizome, 3 parts of pericarpium citri reticulatae viride;

auxiliary materials: 100-110 parts of water, 4-5 parts of glycerin, 1-1.5 parts of xanthan gum, 1-1.5 parts of vegetable oil, 1-2 parts of squalene, 5-6 parts of emulsifier, 0.5-1 parts of polysorbate-20, 0.5-1 parts of triethanolamine, 0.5-1 parts of panthenol, 0.1-0.5 parts of thymopenti and 2-3 parts of honey.

The following preparation is carried out according to the above-mentioned ratio of the topical drug for treating breast cancer, comprising the following steps:

(1) mixing *Astragalus, Oldenlandia diffusa*, dandelion, *Lycoris radiate, Carapax trionycis, Pinellia pedatisecta, Acorus calamus, Ferula sinkiangensis*, doubleteeth pubescent angelica root, *Cryptotaenia japonica* Hassk, *Whitmania pigra* Whitman, *Wedelia chinensis, Echinacea purpurea, Folium Eriobotryae, Sedum sarmentosum, Angelicae sinensis, asparagus*, scorpio, *Rubia cordifolia* L., myrrh, nutgrass galingale rhizome and pericarpium citri reticulatae viride together; adding water into the mixture of those components, in which the weight of the water is 4-5 times the weight of all the mixture; after soaking the mixture at room temperature for 20-25 minutes, decocting it at 80-90° C. for 100-150 minutes; then filtering it to get the filtrate and dregs for later use;

(2) adding 50-60% ethanol solution to the dregs obtained by step (1), in which the weight of the ethanol solution is 4-5 times the weight of the dregs; decocting the mixture at 60-70° C. for 120-160 minutes; then filtering it to get the filtrate and dregs for later use;

(3) heating the filtrate obtained by step (2) to 80-90° C.; and recovering the ethanol and getting the filtrate;

(4) adding 15-18% acetic acid solution to the dregs obtained by step (2), in which the weight of the acetic acid solution is 4-5 times the weight of the dregs; decocting the mixture at 40-50° C. for 50-70 minutes; then filtering it to get the filtrate;

(5) letting the temperature of the filtrate obtained by step (1) and step (3) down to 40-50° C., then mixing them with the filtrate obtained by step (4); adding alfalfa extract and extract of Jew's ear from mulberry trees to the combined filtrate; heating and stirring the mixed solution at 40-50° C. until its weight is 1.5-2 times the weight of all herbs; and treating the mixed solution with small molecule cutting technology to retain its activity and effectiveness;

(6) weighing 100-110 parts by weight of water, 4-5 parts by weight of glycerin and 1-1.5 parts by weight of xanthan gum; dissolving and mixing them together; heating the mixed solution to 80° C.; and sterilizing it;

(7) weighing 1-1.5 parts by weight of vegetable oil, 1-2 parts by weight of squalene, 5-6 parts by weight of emulsifier, 0.5-1 parts by weight of polysorbate-20, 0.5-1 parts by weight of triethanolamine, 0.5-1 parts by weight of panthenol and 0.1-0.5 parts by weight of thymopentin; mixing them; then heating the mixed solution to 80° C.;

(8) mixing the solution obtained by step (6) and step (7) and stirring evenly; when the mixture being cooled to 40-50° C., adding 2-3 parts by weight of honey and stirring evenly; then keeping the mixed solution at the current temperature for 20-25 minutes;

(9) mixing the solution obtained by step (5) and step (8); then keeping stirring the mixture until its temperature falls to room temperature; and

(10) standing the mixture obtained by step (9), then testing and filling to obtain the finished product.

Example 2

A topical drug for treating breast cancer comprises the following components in parts by weight:

8 parts of *Astragalus*, 4 parts of *Oldenlandia diffusa*, 4 parts of dandelion, 7 parts of *Lycoris radiate*, 6 parts of *Carapax trionycis*, 4 parts of *Pinellia pedatisecta*, 2.5 parts of *Acorus calamus*, 4 parts of *Ferula sinkiangensis*, 4 parts of doubleteeth pubescent angelica root, 5 parts of *Cryptotaenia japonica* Hassk, 4 parts of *Whitmania pigra* Whitman, 6 parts of *Wedelia chinensis*, 7 parts of *Echinacea purpurea*, 5 parts of *Folium Eriobotryae*, 4 parts of *Sedum sarmentosum*, 8 parts of *Angelicae sinensis*, 3 parts of *asparagus*, 2 parts of scorpio, 7 parts of *Rubia cordifolia* L., 2 parts of alfalfa extract, 4 parts of extract of Jew's ear from mulberry trees, 6 parts of myrrh, 5 parts of nutgrass galingale rhizome and 5 parts of pericarpium citri reticulatae viride;

auxiliary materials: 100-110 parts of water, 4-5 parts of glycerin, 1-1.5 parts of xanthan gum, 1-1.5 parts of vegetable oil, 1-2 parts of squalene, 5-6 parts of emulsifier, 0.5-1 parts of polysorbate-20, 0.5-1 parts of triethanolamine, 0.5-1 parts of panthenol, 0.1-0.5 parts of thymopenti and 2-3 parts of honey.

The following preparation is carried out according to the above-mentioned ratio of the topical drug for treating breast cancer, comprising the following steps:

(1) mixing *Astragalus, Oldenlandia diffusa*, dandelion, *Lycoris radiate, Carapax trionycis, Pinellia pedatisecta, Acorus calamus, Ferula sinkiangensis*, doubleteeth pubescent angelica root, *Cryptotaenia japonica* Hassk, *Whitmania pigra* Whitman, *Wedelia chinensis, Echinacea purpurea, Folium Eriobotryae, Sedum sarmentosum, Angelicae sinensis, asparagus*, scorpio, *Rubia cordifolia* L., myrrh, nutgrass galingale rhizome and pericarpium citri reticulatae viride together; adding water into the mixture of those components, in which the weight of the water is 4-5 times the weight of all the mixture; after soaking the mixture at room temperature for 20-25 minutes, decocting it at 80-90° C. for 100-150 minutes; then filtering it to get the filtrate and dregs for later use;

(2) adding 50-60% ethanol solution to the dregs obtained by step (1), in which the weight of the ethanol solution is 4-5 times the weight of the dregs; decocting the mixture at 60-70° C. for 120-160 minutes; then filtering it to get the filtrate and dregs for later use;

(3) heating the filtrate obtained by step (2) to 80-90° C.; and recovering the ethanol and get the filtrate;

(4) adding 15-18% acetic acid solution to the dregs obtained by step (2), in which the weight of acetic acid solution is 4-5 times the weight of the dregs; decocting the mixture at 40-50° C. for 50-70 minutes; then filtering it to get the filtrate;

(5) letting the temperature of the filtrate obtained by step (1) and step (3) down to 40-50° C., then mixing them with the filtrate obtained by step (4); adding alfalfa extract and extract of Jew's ear from mulberry trees to the combined filtrate; heating and stirring the mixed solution at 40-50° C. until its weight is 1.5-2 times the weight of all herbs; and treating the mixed solution with small molecule cutting technology to retain its activity and effectiveness;

(6) weighing 100-110 parts by weight of water, 4-5 parts by weight of glycerin and 1-1.5 parts by weight of xanthan gum; dissolving and mixing them together; heating the mixed solution to 80° C.; and sterilizing it;

(7) weighing 1-1.5 parts by weight of vegetable oil, 1-2 parts by weight of squalene, 5-6 parts by weight of emulsifier, 0.5-1 parts by weight of polysorbate-20, 0.5-1 parts by weight of triethanolamine, 0.5-1 parts by weight of panthenol and 0.1-0.5 parts by weight of thymopentin; mixing them; then heating the mixed solution to 80° C.;

(8) mixing the solution obtained by step (6) and step (7) and stirring evenly; when the mixture being cooled to 40-50° C., adding 2-3 parts by weight of honey and stir ring evenly; then keeping the mixed solution at the current temperature for 20-25 minutes;

(9) mixing the solution obtained by step (5) and step (8); then keeping stirring the mixture until its temperature falls to room temperature; and

(10) standing the mixture obtained by step (9), then testing and filling to obtain the finished product.

Example 3

A topical drug for treating breast cancer comprises the following components in parts by weight:

10 parts of *Astragalus*, 5 parts of *Oldenlandia diffusa*, 5 parts of dandelion, 10 parts of *Lycoris radiate*, 8 parts of *Carapax trionycis*, 5 parts of *Pinellia pedatisecta*, 3 parts of *Acorus calamus*, 5 parts of *Ferula sinkiangensis*, 5 parts of doubleteeth pubescent angelica root, 6 parts of *Cryptotaenia japonica* Hassk, 5 parts of *Whitmania pigra* Whitman, 8 parts of *Wedelia chinensis*, 8 parts of *Echinacea purpurea*, 6 parts of *Folium Eriobotryae*, 5 parts of *Sedum sarmentosum*, 10 parts of *Angelicae sinensis*, 5 parts of *asparagus*, 3 parts of scorpio, 8 parts of *Rubia cordifolia* L., 3 parts of alfalfa extract, 5 parts of extract of Jew's ear from mulberry trees, 7 parts of myrrh, 6 parts of nutgrass galingale rhizome, 5 parts of pericarpium citri reticulatae viride;

auxiliary materials: 100-110 parts of water, 4-5 parts of glycerin, 1-1.5 parts of xanthan gum, 1-1.5 parts of vegetable oil, 1-2 parts of squalene, 5-6 parts of emulsifier, 0.5-1 parts of polysorbate-20, 0.5-1 parts of triethanolamine, 0.5-1 parts of panthenol, 0.1-0.5 parts of thymopenti and 2-3 parts of honey.

The following preparation is carried out according to the above-mentioned ratio of the topical drug for treating breast cancer, comprising the following steps:

(1) mixing *Astragalus, Oldenlandia diffusa*, dandelion, *Lycoris radiate, Carapax trionycis, Pinellia pedatisecta, Acorus calamus, Ferula sinkiangensis*, doubleteeth pubescent angelica root, *Cryptotaenia japonica* Hassk, *Whitmania pigra* Whitman, *Wedelia chinensis, Echinacea purpurea, Folium Eriobotryae, Sedum sarmentosum, Angelicae sinensis, asparagus*, scorpio, *Rubia cordifolia* L., myrrh, nutgrass galingale rhizome and pericarpium citri reticulatae viride together; adding water into the mixture of those components, in which the is weight of the water is 4-5 times the weight of all the mixture; after soaking the mixture at room temperature for 20-25 minutes, decocting it at 80-90° C. for 100-150 minutes; then filtering it to get the filtrate and dregs for later use;

(2) adding 50-60% ethanol solution to the dregs obtained by step (1), in which the weight of the ethanol solution is 4-5 times the weight of the dregs; decocting the mixture at 60-70° C. for 120-160 minutes; then filtering it to get the filtrate and dregs for later use;

(3) heating the filtrate obtained by step (2) to 80-90° C.; and recovering the ethanol and getting the filtrate;

(4) adding 15-18% acetic acid solution to the dregs obtained by step (2), in which the weight of acetic acid solution is 4-5 times the weight of the dregs; decocting the mixture at 40-50° C. for 50-70 minutes; then filtering it to get the filtrate;

(5) letting the temperature of the filtrate obtained by step (1) and step (3) down to 40-50° C., then mixing them with the filtrate obtained by step (4); adding alfalfa extract and extract of Jew's ear from mulberry trees to the combined filtrate; heating and stirring the mixed solution at 40-50° C. until its weight is 1.5-2 times the weight of all herbs; and treating the mixed solution with small molecule cutting technology to retain its activity and effectiveness;

(6) weighing 100-110 parts by weight of water, 4-5 parts by weight of glycerin and 1-1.5 parts by weight of xanthan gum; dissolving and mixing them together; heating the solution to 80° C.; and sterilizing it;

(7) weighing 1-1.5 parts by weight of vegetable oil, 1-2 parts by weight of squalene, 5-6 parts by weight of emulsifier, 0.5-1 parts by weight of polysorbate-20, 0.5-1 parts by weight of triethanolamine, 0.5-1 parts by weight of panthenol and 0.1-0.5 parts by weight of thymopentin; mixing them; then heating the mixed solution to 80° C.;

(8) mixing the solution obtained by step (6) and step (7) and stirring evenly; when the mixture being cooled to 40-50° C., adding 2-3 parts by weight of honey and stirring evenly; then keeping the mixed solution at the current temperature for 20-25 minutes;

(9) mixing the solution obtained by step (5) and step (8); then keeping stirring the mixture until its temperature falls to room temperature; and

(10) standing the mixture obtained by step (9) stable, then testing and filling to obtain the finished product.

Example 4

A topical drug for treating breast cancer comprises the following components in parts by weight:

8 parts of *Astragalus*, 4 parts of *Oldenlandia diffusa*, 4 parts of dandelion, 7 parts of *Lycoris radiate*, 6 parts of *Carapax trionycis*, 4 parts of *Pinellia pedatisecta*, 2.5 parts of *Acorus calamus*, 4 parts of *Ferula sinkiangensis*, 4 parts of doubleteeth pubescent angelica root, 5 parts of *Cryptotaenia japonica* Hassk, 4 parts of *Whitmania pigra* Whitman, 6 parts of *Wedelia chinensis*, 7 parts of *Echinacea purpurea*, 5 parts of Folium Eriobotryae, 4 parts of *Sedum sarmentosum*, 8 parts of *Angelicae sinensis*, 3 parts of *asparagus*, 2 parts of scorpio, 7 parts of *Rubia cordifolia* L., 2 parts of alfalfa extract, 4 parts of extract of Jew's ear from mulberry trees, 6 parts of myrrh, 5 parts of nutgrass galingale rhizome and 5 parts of pericarpium citri reticulatae viride;

auxiliary materials: 100-110 parts of water, 4-5 parts of glycerin, 1-1.5 parts of xanthan gum, 1-1.5 parts of vegetable oil, 1-2 parts of squalene, 5-6 parts of emulsifier, 0.5-1 parts of polysorbate-20, 0.5-1 parts of triethanolamine, 0.5-1 parts of panthenol, 0.1-0.5 parts of thymopenti and 2-3 parts of honey.

The following preparation is carried out according to the above-mentioned ratio of the topical drug for treating breast cancer, comprising the following steps:

(1) mixing *Astragalus, Oldenlandia diffusa*, dandelion, *Lycoris radiate, Carapax trionycis, Pinellia pedatisecta, Acorus calamus, Ferula sinkiangensis*, doubleteeth pubescent angelica root, *Cryptotaenia japonica* Hassk, *Whitmania pigra* Whitman, *Wedelia chinensis, Echinacea purpurea, Folium Eriobotryae, Sedum sarmentosum, Angelicae sinensis, asparagus*, scorpio, *Rubia cordifolia* L., myrrh, nutgrass galingale rhizome and pericarpium citri reticulatae viride together; adding water into the mixture of those components, in which the weight of the water is 4-5 times the weight of all the mixture; decocting it for 100-150 minutes; then filtering it to get the filtrate and dregs for later use;

(2) adding 50-60% ethanol solution to the dregs obtained by step (1), in which the weight of the ethanol solution is 4-5 times the weight of the dregs; decocting the mixture for 120-160 minutes; then filtering it to get the filtrate and dregs for later use;

(3) heating the filtrate obtained by step (2) to 80-90° C.; and recovering the ethanol and getting the filtrate;

(4) adding acetic acid solution to the dregs obtained by step (2), in which the weight of acetic acid solution is 4-5 times the weight of the dregs; decocting the mixture for 50-70 minutes; then filtering it to get the filtrate;

(5) combining the filtrate obtained by step (1), step (3) and step (4); add alfalfa extract and extract of Jew's ear from mulberry trees to the combined filtrate; heating and stirring the mixed solution at 40-50° C. until its weight is 1.5-2 times the weight of all herbs; and treating the mixed solution with small molecule cutting technology to retain its activity and effectiveness;

(6) weighing 100-110 parts by weight of water, 4-5 parts by weight of glycerin and 1-1.5 parts by weight of xanthan gum; dissolving and mixing them together; then heating the mixed solution to 80° C.; and sterilizing it;

(7) weighing 1-1.5 parts by weight of vegetable oil, 1-2 parts by weight of squalene, 5-6 parts by weight of emulsifier, 0.5-1 parts by weight of polysorbate-20, 0.5-1 parts by weight of triethanolamine and 0.5-1 parts by weight of panthenol; mixing them; then heating the mixed solution to 80° C.;

(8) mixing the solution obtained by step (6) and step (7) and stirring evenly; when the mixture being cooled to 40-50° C., adding 2-3 parts by weight of honey and stirring evenly; then keeping the mixed solution at the current temperature for 20-25 minutes;

(9) mixing the solution obtained by step (5) and step (8); then keeping stirring the mixture until its temperature falls to room temperature; and

(10) standing the mixture obtained by step (9), then testing and filling to is obtain the finished product.

Example 5

A topical drug for treating breast cancer comprises the following components in parts by weight:

8 parts of *Astragalus,* 4 parts of *Oldenlandia diffusa,* 4 parts of dandelion, 7 parts of *Lycoris radiate,* 6 parts of *Carapax trionycis,* 4 parts of *Pinellia pedatisecta,* 2.5 parts of *Acorus calamus,* 4 parts of *Ferula sinkiangensis,* 4 parts of doubleteeth pubescent angelica root, 5 parts of *Cryptotaenia japonica* Hassk, 4 parts of *Whitmania pigra* Whitman, 6 parts of *Wedelia chinensis,* 7 parts of *Echinacea purpurea,* 5 parts of *Folium Eriobotryae,* 4 parts of *Sedum sarmentosum,* 8 parts of *Angelicae sinensis,* 3 parts of *asparagus,* 2 parts of scorpio, 7 parts of *Rubia cordifolia* L., 2 parts of alfalfa extract, 4 parts of extract of Jew's ear from mulberry trees, 6 parts of myrrh, 5 parts of nutgrass galingale rhizome and 5 parts of pericarpium citri reticulatae viride;

auxiliary materials: 100-110 parts of water, 4-5 parts of glycerin, 1-1.5 parts of xanthan gum, 1-1.5 parts of vegetable oil, 1-2 parts of squalene, 5-6 parts of emulsifier, 0.5-1 parts of polysorbate-20, 0.5-1 parts of triethanolamine, 0.5-1 parts of panthenol, 0.1-0.5 parts of thymopenti and 2-3 parts of honey.

The following preparation is carried out according to the above-mentioned ratio of the topical drug for treating breast cancer, comprising the following steps:

(1) mixing *Astragalus, Oldenlandia diffusa,* dandelion, *Lycoris radiate, Carapax trionycis, Pinellia pedatisecta, Acorus calamus, Ferula sinkiangensis,* doubleteeth pubescent angelica root, *Cryptotaenia japonica* Hassk, *Whitmania pigra* Whitman, *Wedelia chinensis, Echinacea purpurea, Folium Eriobotryae, Sedum sarmentosum, Angelicae sinensis, asparagus,* scorpio, *Rubia cordifolia* L., myrrh, nutgrass galingale rhizome and pericarpium citri reticulatae viride together; adding water into the mixture of those components, in which the weight of water is 4-5 times the weight of all the mixture; after soaking the mixture at room temperature for 20-25 minutes, decocting it at 80-90° C. for 100-150 minutes; then filtering it to get the filtrate and dregs for later use;

(2) adding 50-60% ethanol solution to the dregs obtained by step (1), in which the weight of the ethanol solution is 4-5 times the weight of the dregs; decocting the mixture at 60-70° C. for 120-160 minutes; then filtering it to get the filtrate and dregs for later use;

(3) heating the filtrate obtained by step (2) to 80-90° C.; and recovering the ethanol and getting the filtrate;

(4) adding 15-18% acetic acid solution to the dregs obtained by step (2), in which the weight of acetic acid solution is 4-5 times the weight of the dregs; decocting the mixture at 40-50° C. for 50-70 minutes; then filtering it to get the filtrate;

(5) letting the temperature of the filtrate obtained by step (1) and step (3) down to 40-50° C., then mixing them with the filtrate obtained by step (4); adding alfalfa extract and extract of Jew's ear from mulberry trees to the combined filtrate; heating and stirring the mixed solution at 40-50° C. until its is weight is 1.5-2 times the weight of all herbs;

(6) weighing 100-110 parts by weight of water, 4-5 parts by weight of glycerin and 1-1.5 parts by weight of xanthan gum; dissolving and mixing them together; heating the mixed solution to 80° C.; and sterilizing it;

(7) weighing 1-1.5 parts by weight of vegetable oil, 1-2 parts by weight of squalene, 5-6 parts by weight of emulsifier, 0.5-1 parts by weight of polysorbate-20, 0.5-1 parts by weight of triethanolamine, 0.5-1 parts by weight of panthenol and 0.1-0.5 parts by weight of thymopentin; mixing them; then heating the mixed solution to 80° C.;

(8) mixing the solution obtained by step (6) and step (7) and stirring evenly; when the mixture being cooled to 40-50° C., adding 2-3 parts by weight of honey and stirring evenly; then keeping the mixed solution at the current temperature for 20-25 minutes;

(9) mixing the solution obtained by step (5) and step (8); then keeping stirring the mixture until its temperature falls to room temperature; and

(10) standing the mixture obtained by step (9), then testing and filling to obtain the finished product.

After used the topical drugs for treating breast cancer prepared in Example 1-3, the lumps on patients disappeared or significantly reduced, and the recurrence of breast cancer metastasis is significantly reduced and the cure rate of breast cancer has been effectively improved. Owing to not controlling the temperature of extraction process in Example 4 and not using is small molecule cutting technology for drug treatment in Example 5, the cure rates of breast cancer by Example 4 and 5 declined.

The topical drugs for treating breast cancer and the preparation methods thereof provided by the examples have been described in detail above. The principles and implementation methods of this invention have been expatiated by certain embodiments. The description of the embodiments above is only intended to help to understand the method and the core concept of this invention. Meanwhile, to those generally skilled in the art, the specific implementation ways and application scope can be changed according to the concept of this invention. In conclusion, the contents of this specification should not be construed to a limitation of the present invention.

The invention claimed is:

1. A topical drug for treating breast cancer, wherein, the said topical drug for treating breast cancer comprises the following components in parts by weight:

5-10 parts of *Astragalus*, 3-5 parts of *Oldenlandia diffusa*, 3-5 parts of dandelion, 5-10 parts of *Lycoris radiate*, 5-8 parts of *Carapax trionycis*, 3-5 parts of *Pinellia pedatisecta*, 2-3 parts of *Acorus calamus*, 3-5 parts of *Ferula sinkiangensis*, 3-5 parts of doubleteeth pubescent angelica root, 4-6 parts of *Cryptotaenia japonica* Hassk, 3-5 parts of *Whitmania pigra* Whitman, 5-8 parts of *Wedelia chinensis*, 6-8 parts of *Echinacea purpurea*, 4-6 parts of *Folium Eriobotryae*, 3-5 parts of *Sedum sarmentosum*, 5-10 parts of *Angelicae sinensis*, 2-5 parts of asparagus, 2-3 parts of scorpio, 5-8 parts of *Rubia cordifolia* L., 2-3 parts of alfalfa extract, 3-5 parts of extract of Jew's ear from mulberry trees, 5-7 parts of myrrh, 3-6 parts of nutgrass galingale rhizome and 3-5 parts of pericarpium citri reticulatae viride.

2. The topical drug for treating breast cancer according to claim 1, wherein, the said topical drug for treating breast cancer comprises the following components in parts by weight:

8 parts of *Astragalus*, 4 parts of *Oldenlandia diffusa*, 4 parts of dandelion, 7 parts of *Lycoris radiate*, 6 parts of *Carapax trionycis*, 4 parts of *Pinellia pedatisecta*, 2.5 parts of *Acorus calamus*, 4 parts of *Ferula sinkiangensis*, 4 parts of doubleteeth pubescent angelica root, 5 parts of *Cryptotaenia japonica* Hassk, 4 parts of *Whitmania pigra* Whitman, 6 parts of *Wedelia chinensis*, 7 parts of *Echinacea purpurea*, 5 parts of *Folium Eriobotryae*, 4 parts of *Sedum sarmentosum*, 8 parts of *Angelicae sinensis*, 3 parts of asparagus, 2 parts of scorpio, 7 parts of *Rubia cordifolia* L., 2 parts of alfalfa extract, 4 parts of extract of Jew's ear from mulberry trees, 6 parts of myrrh, 5 parts of nutgrass galingale rhizome and 5 parts of pericarpium citri reticulatae viride.

3. The topical drug for treating breast cancer according to claim 1, wherein, the said topical drug for treating breast cancer comprises the following auxiliary materials in parts by weight:

100-110 parts of water, 4-5 parts of glycerin, 1-1.5 parts of xanthan gum, 1-1.5 parts of vegetable oil, 1-2 parts of squalene, 5-6 parts of emulsifier, 0.5-1 parts of polysorbate-20, 0.5-1 parts of triethanolamine, 0.5-1 parts of panthenol, 0.1-0.5 parts of thymopentin and 2-3 parts of honey.

4. A method for preparation of the topical drug for treating breast cancer, wherein, it comprises the following steps:

(1) weighing the following components in parts by weight: 5-10 parts of *Astragalus*, 3-5 parts of *Oldenlandia diffusa*, 3-5 parts of dandelion, 5-10 parts of *Lycoris radiate*, 5-8 parts of *Carapax trionycis*, 3-5 parts of *Pinellia pedatisecta*, 2-3 parts of *Acorus calamus*, 3-5 parts of *Ferula sinkiangensis*, 3-5 parts of doubleteeth pubescent angelica root, 5-6 parts of *Cryptotaenia japonica* Hassk, 3-5 parts of *Whitmania pigra* Whitman, 5-8 parts of *Wedelia chinensis*, 6-8 parts of *Echinacea purpurea*, 4-6 parts of *Folium Eriobotryae*, 3-5 parts of *Sedum sarmentosum*, 5-10 parts of *Angelicae sinensis*, 2-5 parts of asparagus, 2-3 parts of scorpio, 5-8 parts of *Rubia cordifolia* L., 5-7 parts of myrrh, 3-6 parts of nutgrass galingale rhizome and 3-5 parts of pericarpium citri reticulatae viride; adding water to the mixture of those components, in which the weight of water is 4-5 times the weight of all the above-mentioned components; decocting the mixture for 100-150 minutes; then filtering the mixture to get the filtrate and dregs for later use;

(2) adding ethanol solution to the dregs obtained by step (1), in which the weight of ethanol solution is 4-5 times the weight of the dregs; decocting the mixture for 120-160 minutes; then filtering it to get the filtrate and dregs for later use;

(3) heating the filtrate obtained by step (2) to 80-90° C.; and recovering the ethanol and getting the filtrate;

(4) adding acetic acid solution to the dregs obtained by step (2), in which the weight of acetic acid solution is 4-5 times the weight of the dregs; decocting the mixture for 50-70 minutes; then filtering it to get the filtrate;

(5) combining the filtrate obtained by step (1), step (3) and step (4); then adding 2-3 parts by weight of alfalfa extract and 3-5 parts by weight of extract of Jew's ear from mulberry trees to the combined filtrate; heating and stirring the mixed solution at 40-50° C. until its weight is 1.5-2 times the weight of all herbs;

(6) weighing 100-110 parts by weight of water, 4-5 parts by weight of glycerin and 1-1.5 parts by weight of xanthan gum; dissolving and mixing them together; heating the mixed solution to 80° C.; and sterilizing it;

(7) weighing 1-1.5 parts by weight of vegetable oil, 1-2 parts by weight of squalene, 5-6 parts by weight of emulsifier, 0.5-1 parts by weight of polysorbate-20, 0.5-1 parts by weight of triethanolamine and 0.5-1 parts by weight of panthenol; mixing them; then heating the mixed solution to 80° C.;

(8) mixing the solution obtained by step (6) and step (7) and stirring evenly; when the mixture being cooled to 40-50° C., adding 2-3 parts by weight of honey and stirring evenly; then keeping the mixed solution at the current temperature for 20-25 minutes;

(9) mixing the solution obtained by step (5) and step (8); then keeping stirring the mixture until its temperature falls to room temperature; and

(10) standing the solution obtained by step (9), then testing and filling to obtain the finished product.

5. The method for preparation of the topical drug for treating breast cancer according to claim 4, wherein, in step (1), the mixture is soaked at room temperature for 20-25 minutes after adding 4-5 times water to it; then the mixture is decocted at 80-90° C. for 100-150 minutes.

6. The method for preparation of the topical drug for treating breast cancer according to claim 4, wherein, in step (2), the concentration of the ethanol solution is 50-60% and the decocting temperature is 60-70° C.

7. The method for preparation of the topical drug for treating breast cancer according to claim 4, wherein, in step (4), the concentration of the acetic acid solution is 15-18% and the decocting temperature is 40-50° C.

8. The method for preparation of the topical drug for treating breast cancer according to claim 4, wherein, in step (5), the temperature of the filtrate obtained by step (1) and step (3) is reduced down to room temperature; then the above filtrate is combined with the filtrate obtained by step (4).

9. The method for preparation of the topical drug for treating breast cancer according to claim 4, wherein, the solution obtained by step (5) is treated with small molecule cutting technology to retain its activity and effectiveness simultaneously.

\* \* \* \* \*